(12) United States Patent
Zhou et al.

(10) Patent No.: US 9,820,727 B2
(45) Date of Patent: Nov. 21, 2017

(54) SINGLE PIECE, DUAL COMPONENT SEALING PAD AND METHODS

(75) Inventors: Zhengrong Zhou, Shanghai (CN); Anna Norlin-Weissenrieder, Stockholm (SE); Stephanie M. Board, West St. Paul, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 1000 days.

(21) Appl. No.: 13/391,878

(22) PCT Filed: Aug. 20, 2010

(86) PCT No.: PCT/US2010/002292
§ 371 (c)(1),
(2), (4) Date: Aug. 20, 2012

(87) PCT Pub. No.: WO2011/025529
PCT Pub. Date: Mar. 3, 2011

(65) Prior Publication Data
US 2012/0310275 A1 Dec. 6, 2012

Related U.S. Application Data

(60) Provisional application No. 61/236,472, filed on Aug. 24, 2009.

(51) Int. Cl.
*A61B 17/03* (2006.01)
*A61B 17/00* (2006.01)
*A61B 17/34* (2006.01)

(52) U.S. Cl.
CPC .. *A61B 17/0057* (2013.01); *A61B 2017/0065* (2013.01); *A61B 2017/00637* (2013.01); *A61B 2017/00654* (2013.01); *A61B 2017/00898* (2013.01); *A61B 2017/347* (2013.01)

(58) Field of Classification Search
CPC ...... A61B 17/0057; A61B 2017/00637; A61B 2017/347; A61B 2017/00654; A61B 2017/00898; A61B 2017/0065
USPC .................................. 606/158, 213
See application file for complete search history.

(56) References Cited

U.S. PATENT DOCUMENTS

| | | |
|---|---|---|
| 5,179,963 A | 1/1993 | Berger |
| 5,326,350 A | 7/1994 | Li |
| 5,591,204 A * | 1/1997 | Janzen et al. ............... 606/213 |
| 5,741,223 A | 4/1998 | Janzen et al. |
| 6,045,569 A | 4/2000 | Kensey et al. |

(Continued)

OTHER PUBLICATIONS

PCT International Search Report for International Application No. PCT/US2010/002292, dated Oct. 28, 2010.

*Primary Examiner* — Vy Bui
(74) *Attorney, Agent, or Firm* — Holland & Hart

(57) ABSTRACT

A tissue puncture closure device includes a carrier tube and a sealing plug. The carrier tube includes a distal end configured for insertion into the tissue puncture. The sealing plug is positioned in the carrier tube and arranged for ejection from the distal end of the carrier tube into the tissue puncture. The sealing plug includes a first collagen portion having a first cross-linked chemical structure, and a second collagen portion positioned proximal of the first collagen portion in the carrier tube. The second collagen portion has a second cross-linked chemical structure that is different from the first cross-linked chemical structure.

14 Claims, 15 Drawing Sheets

(56) References Cited

U.S. PATENT DOCUMENTS

| | | | |
|---|---|---|---|
| 6,090,130 A | 7/2000 | Nash et al. | |
| 7,955,353 B1 * | 6/2011 | Ashby | A61L 31/146 606/108 |
| 8,382,794 B2 * | 2/2013 | Belhe et al. | 606/213 |
| 2006/0034930 A1 | 2/2006 | Khosravi et al. | |

* cited by examiner

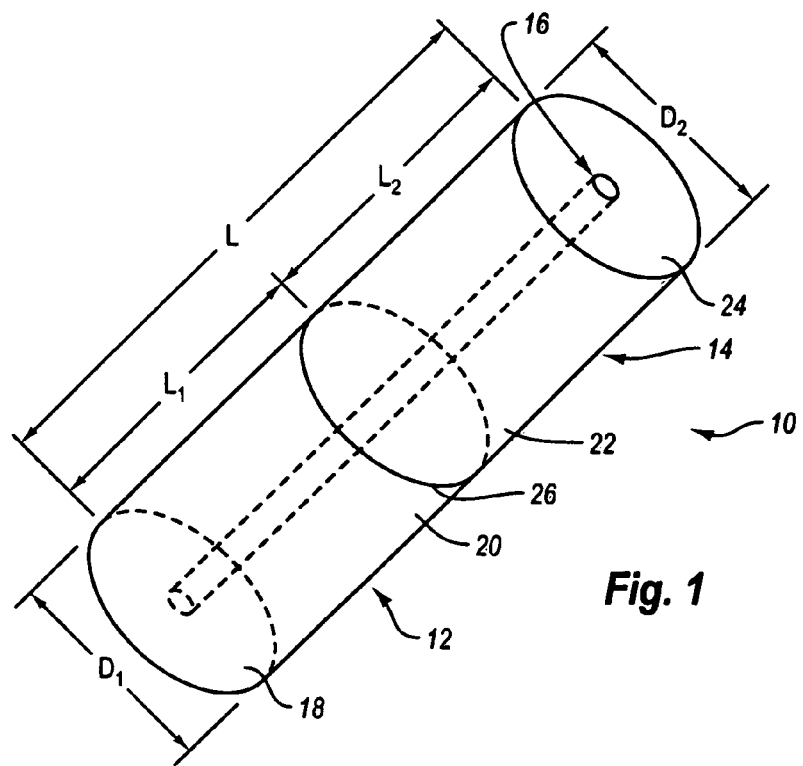
Fig. 1
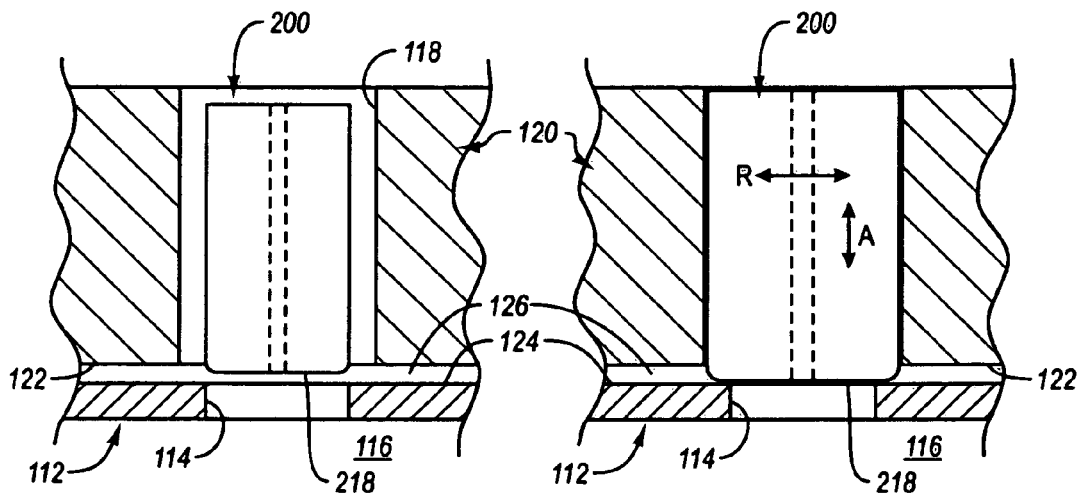
Fig. 2  Fig. 3

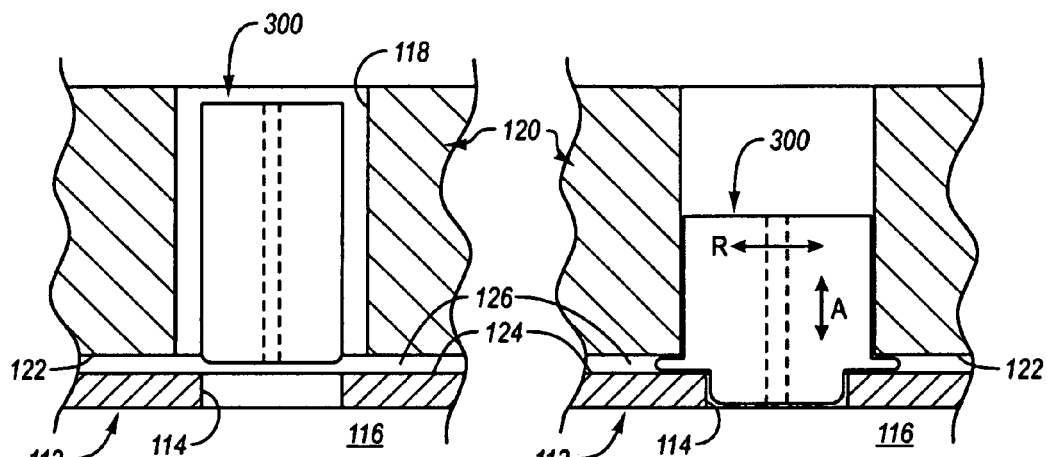
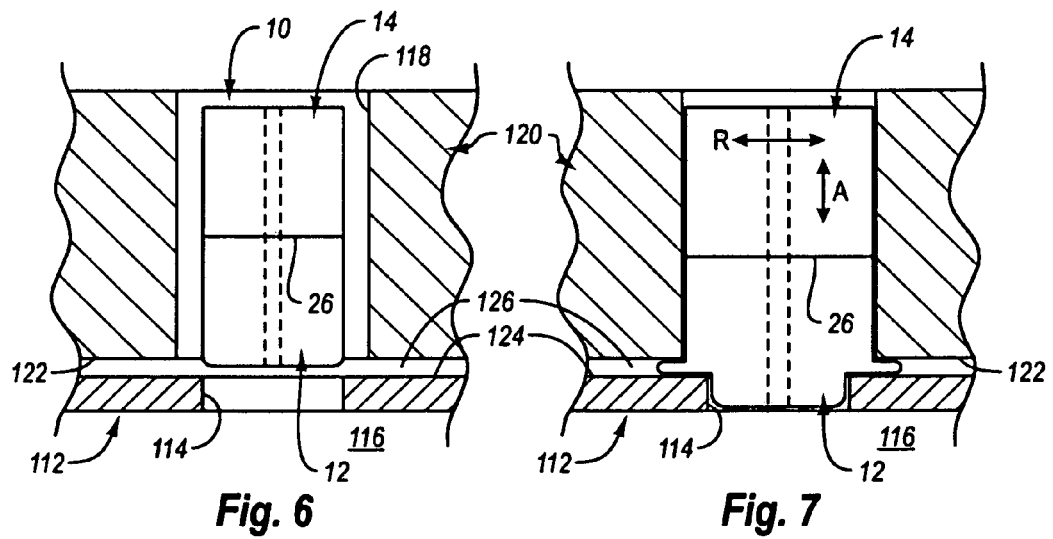

SINGLE PIECE, DUAL COMPONENT SEALING PAD AND METHODS

RELATED APPLICATION

This application claims the benefit of U.S. Provisional Patent Application No. 61/236,472, filed Aug. 24, 2009, which is hereby incorporated by reference herein in its entirety.

TECHNICAL FIELD

The present disclosure relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130; and 6,045,569, which are hereby incorporated in their entireties by this reference.

Typical closure devices such as the ones described in the above-mentioned patents place a sealing plug at the tissue puncture site. Nevertheless, the incision track leading to the invaded artery often continues to ooze blood from side vessels at the puncture site. Manual compression is typically applied at the puncture site to stop the track bleeding. Manual compression can lead to patient soreness and requires additional time from medical personnel. The time spent by medical personnel compressing the puncture site to stop the bleeding from the incision track can be expensive to the patient, and tiring to the medical personnel. Accordingly, there is a need for improving the sealing methods and apparatus at the site of subcutaneous tissue punctures.

SUMMARY

The present disclosure addresses the above-described needs and others. Specifically, the present disclosure is directed to devices, methods and systems for closing tissue punctures. One aspect of the present disclosure is directed to a tissue puncture closure device for partial insertion into and sealing of a tissue puncture. The tissue puncture closure device includes a carrier tube and a sealing plug. The carrier tube includes a distal end configured for insertion into the tissue puncture. The sealing plug is positioned in the carrier tube and arranged for ejection from the distal end of the carrier tube into the tissue puncture. The sealing plug includes a first collagen portion having a first cross-linked chemical structure, and a second collagen portion positioned proximal of the first collagen portion in the carrier tube. The second collagen portion may have a second cross-linked chemical structure that is different from the first cross-linked chemical structure.

The first collagen portion may be connected to the second collagen portion to define a single piece sealing pad. At least a portion of the first collagen portion may be positioned radially of the second collagen portion. The first collagen portion may include a substantially uncross-linked chemical structure and the second collagen portion may include a more cross-linked chemical structure than the first collagen portion. The sealing pad may include at least one aperture that extends from a distal end to a proximal end of the sealing pad. The first and second collagen portions may have different lengths in a longitudinal direction. The first collagen portion may be configured to change into a gel or semi-gel state when exposed to liquid, and the second collagen portion may be configured to expand when exposed to liquid. The tissue puncture closure device may further include a guidewire that extends through the sealing pad and the tissue puncture.

Another aspect of the present disclosure relates to a single piece sealing pad for use in sealing a tissue puncture. The sealing pad includes a first collagen portion and a second collagen portion connected to the first collagen portion. The second collagen portion may have a more cross-linked chemical structure than that of the first collagen portion. The sealing pad may have a cylindrical construction with a generally circular cross-sectional shape. The first collagen portion may have a length that is less than a length of the second collagen portion. The first collagen portion may include a substantially uncross-linked chemical structure and the second collagen portion may include a substantially cross-linked chemical structure. The sealing pad may further include an aperture that extends through the first and second collagen portions along a central axis of the single piece sealing pad. The first and second collagen portions may be connected with a chemical bond.

A further aspect of the present disclosure relates to a method of sealing a tissue puncture in an internal tissue wall accessible through a percutaneous incision. The method may include providing a tissue puncture closure device that includes a sealing pad, the sealing pad having a distal portion and a proximal portion that have different cross-linked chemical structures, and deploying the sealing pad in the percutaneous incision adjacent to the tissue puncture. The method may also include absorbing liquid into the distal and proximal portions of the sealing pad, wherein the distal portion at least partially flows into the tissue puncture, and the proximal portion expands radially outward into engagement with a sidewall of the percutaneous incision.

The distal portion of the sealing pad may have a less cross-linked chemical structure than the proximal portion of the sealing pad. The distal portion may retain a solid state prior to absorbing liquid and change to a gel or semi-gel state after absorbing liquid. The distal portion may flow into a space defined between an outer surface of a vessel that defines the vessel puncture and an inner surface of a tissue layer that defines the percutaneous incision.

Another aspect of the present disclosure relates to a method of forming a sealing plug that includes providing a mold cavity, partially filling the mold cavity with a first collagen slurry, curing the first collagen slurry to provide a first collagen portion having a first cross-linked chemical structure, at least partially filling the mold cavity with a second collagen slurry in contact with the first collagen portion, and curing the second collagen slurry to provide a second collagen portion having a second cross-linked chemical structure that is different from the first cross-linked chemical structure.

The first cross-linked chemical structure may be more cross-linked than the second cross-linked chemical structure. Curing at least one of the first and second collagen slurries may include freeze-drying the at least one of the first and second collagen slurries. The method may further include providing an elongate pin in the mold prior to filling the mold cavity, wherein the elongate pin defines an aperture in the sealing plug.

Additional advantages and novel features will be set forth in the description which follows or may be learned by those skilled in the art through reading these materials or practicing the invention. Some advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples and do not limit the scope of the present disclosure.

FIG. 1 is a prospective view of an example sealing pad in accordance with the present disclosure.

FIG. 2 is a cross-sectional side view of another example sealing pad in an unexpanded state positioned in an incision tract.

FIG. 3 is a cross-sectional view of the sealing pad of FIG. 2 in an expanded state.

FIG. 4 is a cross-sectional view of another example sealing pad in an unexpanded state in an incision tract.

FIG. 5 is a cross-sectional view of the sealing pad of FIG. 4 in an expanded state.

FIG. 6 is a cross-sectional view of the sealing pad of FIG. 1 in an unexpanded state in a tissue tract.

FIG. 7 is a cross-sectional view of the sealing pad of FIG. 6 in an expanded state.

Throughout the drawings, identical reference numbers designate similar, but not necessarily identical, elements.

DETAILED DESCRIPTION

Figure 10:
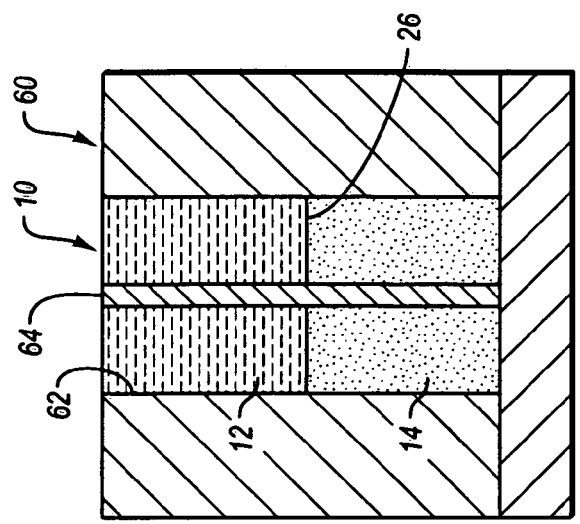
FIG. 10 is a cross-sectional view of the mold cavity of FIG. 9 with an additional sealing pad material included therein.

The present disclosure describes techniques and apparatus for closing an internal tissue wall puncture, preferably using a closure device and an insertion sheath, while reducing the likelihood of leaks. The reduction in the likelihood of leaks is facilitated according to some embodiments by providing a sealing pad having multiple portions with different chemical structures.

The sealing pad portions may be arranged at specific locations on the sealing pad to provide an improved sealing function for various structures along the internal tissue wall puncture. For example, the internal tissue wall puncture may be defined in part by a percutaneous incision in a tissue layer and a vessel puncture in a vessel wall that are arranged coaxial with each other. In some instances, a gap or space exists between an outer surface of the vessel wall and an inner surface of the tissue layer.

The sealing pad may include a first portion arranged in the tissue puncture adjacent to the gap and the vessel puncture. The sealing pad may also include a second portion arranged within the percutaneous incision, typically proximal of the first portion. The first portion has a first cross-linked chemical structure that permits at least some flow of the first portion into the gap and the vessel puncture when the first portion is exposed to liquid (i.e., blood). The second portion has a second cross-linked chemical structure different from the first cross-linked chemical structure that provides swelling or expansion of the second portion to provide sealing contact between the second portion and an internal wall of the percutaneous incision. The properties of the different cross-linked chemical structures of the first and second sealing pad portions may provide sealing of the vessel puncture and the percutaneous incision, and may also provide sealing of the gap between the vessel and tissue layer.

While the methods and devices shown and described below include reference to specific insertion sheaths and puncture sealing devices, the application of principles described related to closing a tissue puncture is not limited to these specific devices. The principles described herein may be used to close or seal any interior tissue puncture, particularly punctures or incisions in arteries or other bodily lumens. Therefore, while the description below is directed primarily to vascular procedures, the methods and apparatus may be used according to principles described herein with any lumen to control bleeding.

As used in this specification and the appended claims, the term "tissue" means an aggregation of morphologically similar cells and associated intercellular matter acting together to perform one or more specific functions in a body. A "lumen" is any open space or cavity in a bodily organ, especially in a blood vessel. The words "including" and "having," as used in the specification, including the claims, have the same meaning as the word "comprising."

Referring now to FIG. 1, an example sealing pad 10 in accordance with the present disclosure is shown and described. The sealing pad 10 comprises first and second portions 12, 14. In some arrangements, the first portion 12 is positioned distal of the second portion 14 and referred to as a distal portion. Second portion 14 may be referred to herein as a proximal portion 14. The first portion 12 includes a distal end 18 and a proximal end 20. The second portion 14 includes a distal end 22 and a proximal end 24. A connection point 26 (also referred to as a connection interface 26) may be defined between the first and second portions 12, 14. An aperture 16 may extend from the distal end 18 of the first portion 12 to the proximal end 24 of the second portion 14.

The first and second portions 12, 14 may have a generally cylindrical constructions with lengths $L_1$, $L_2$, respectively. The first and second portions 12, 14 may also have a maximum dimension $D_1$, $D_2$, respectively. In at least some arrangements, the first and second portions 12, 14 have a generally circular cross-sectional shape and the maximum dimension $D_1$, $D_2$ is a maximum diameter. Other cross-sectional shapes are possible including, for example, rectangular, triangular, hexagonal, and oval. The first and second portions 12, 14 may have different cross-sectional shapes. The first and second portions 12, 14 may have cross-sectional shapes that vary along the lengths $L_1$, $L_2$. The lengths $L_1$, $L_2$, cross-sectional shapes, and dimensions $D_1$, $D_2$ of the first and second portions 12, 14 may vary to accommodate different puncture and incision sizes and shapes. In some arrangements, the lengths $L_1$ and $L_2$ are different, while in other arrangements the lengths $L_1$ and $L_2$ are the same. A total length L (see FIG. 1) of the sealing pad 10 may be customized for a particular puncture or incision construction.

The aperture 16 may be constructed with a size and shape to permit passage of an implement such as a locator wire that is used to help position the sealing pad. The sealing pad 10 may include additional apertures positioned at alternative locations on the sealing pad 10 for purposes such as, for example, providing a suture path through a portion of the sealing pad 10.

The first and second portions 12, 14 may comprise materials having different properties. For example, the first and second portions 12, 14 may each include a different chemical structure that varies how much cross-linking is present in the material. The cross-link chemical structure of the material of the first and second portions 12, 14 may influence physical characteristics of the first and second portions 12, 14 when the sealing pad 10 absorbs fluid (i.e., blood).

In at least some arrangements, the sealing pad 10 may comprise collagen material or other biologically resorbable material. Collagen material that has an uncross-linked or less cross-linked chemical structure typically takes on a gel or semi-gel state upon absorbing fluid. A collagen material that has a cross-linked or more cross-linked chemical structure may more typically maintain a solid state when absorbing a liquid. In the case of both uncross-linked and cross-linked collagen materials, some expansion may occur upon absorbing a fluid. In at least some types of collagen material, the more cross-linked the chemical structure, the more the material maintains a solid state when absorbing fluids, whereas the less cross-linked the chemical structure the more the material takes on a gel or semi-gel state when absorbing fluid.

Referring to FIGS. 2 and 3, an example sealing pad 200 having a cross-linked or substantially cross-linked chemical structure is shown and described. The sealing pad 200 is positioned in a percutaneous incision 118 adjacent to a vessel puncture 114 of a vessel 112. The vessel 112 has a vessel interior 116 positioned opposite the sealing pad 200. A space or gap 126 may be defined between a tissue inner surface 122 and a vessel outer surface 124.

FIG. 2 illustrates the sealing pad 200 in an unexpanded state (i.e., prior to absorbing a fluid). Upon absorption of at least some fluid, the sealing pad 200 begins to expand to fill the percutaneous incision 118. Expansion may occur in both a radial direction R and an axial direction A. The generally solid state of the sealing pad 200 provides some structure within the percutaneous incision 118 that supports the tissue. Expansion of the sealing pad 200 may move a distal end 218 of the sealing pad 200 into contact with the vessel 112. Such contact may provide at least some amount of sealing of the vessel puncture 114 that limits blood flow through the vessel puncture 114 into the gap 126 and percutaneous incision 118. In other arrangements, the expanded sealing pad 200 remains out of contact with the vessel 112 thus permitting some blood flow through the vessel puncture 114 into the gap 126. Positioning of the sealing pad 200 within the percutaneous incision 118 relative to the vessel puncture 114 may be particularly important to obtaining proper hemostasis. In at least some arrangements, some oozing and/or hematoma generation may occur if the sealing pad 200 is not properly positioned to provide sealing of the vessel puncture 114 and percutaneous incision 118.

Other advantages associated with using a sealing pad 200 having a cross-linked or substantially cross-linked chemical structure may include, for example, expansion of the sealing pad 200 into a pre-formed shape and size upon absorption of a fluid, predictable mechanical properties and structure within the percutaneous incision, enhanced retention force in a radial direction within the percutaneous incision that maintains the sealing pad 200 in position, a controlled absorption rate and duration when absorbing fluids, and completed regulatory approval for use in commercial products.

Referring now to FIGS. 4 and 5, another example sealing pad 300 having an uncross-linked or substantially uncross-linked chemical structure is shown and described. The sealing pad 300 is positioned within a percutaneous incision 118 adjacent to a vessel puncture 114. The uncross-linked chemical structure of the sealing pad 300 may result in the sealing pad 300 changing to a gel or semi-gel state upon absorption of a fluid.

FIG. 4 illustrates the sealing pad 300 in an unexpanded state prior to absorbing fluid. FIG. 5 illustrates the sealing pad 300 after having absorbed at least some fluid. The gel or semi-gel state of the sealing pad 300 upon absorption of a fluid provides at least some flow of the sealing pad 300 in the radial direction R and axial direction A. In at least some arrangements, portions of the sealing pad 300 may flow into the gap 126 defined between the vessel outer surface 124 and the tissue inner surface 122. At least a portion of the sealing pad 300 may also flow into the vessel puncture 114. Portions of the sealing pad 300 may also move into contact with the inner walls of the percutaneous incision 118. In at least some arrangements, the sealing pad 300, upon absorption of at least some fluid, may provide sealing of the vessel puncture 114, gap 126, and percutaneous incision 118, thereby providing hemostasis of the vessel puncture 114.

An uncross-linked or substantially uncross-linked collagen material may have a reduced time to hemostasis (TTH) than the cross-linked collagen material described above with reference to FIGS. 2 and 3. An uncross-linked collagen material may have a relatively fast transition from a solid state to a gel or semi-gel state that provides the sealing of the vessel puncture 114, gap 126, and percutaneous incision 118 in a reduced time as compared to other materials such as the cross-linked material shown in FIGS. 2 and 3. Further, an uncross-linked collagen material may have a relatively fast rate of absorption of the fluid that may lead to the reduced time to hemostasis. At least some types of available cross-linked collagen materials have already received regulatory approval for treatment of a patient.

Some challenges associated with use of an uncross-linked material in a sealing pad is the limited amount of structural rigidity and mechanical properties within the percutaneous incision 118, a limited amount of retention of force applied to the internal walls of percutaneous incision 118 that otherwise help maintain the sealing pad 300 in position, and a relatively unpredictable time for bioabsorption of the fluid. Further, a tendency of the uncross-linked material to flow while in a gel or semi-gel state presents the potential for the material to flow through the vessel puncture 114 into the vessel interior 116. An adequate seal is typically needed within the vessel interior 116 adjacent to the vessel puncture 114 to limit flow of the material into the vessel 112. An anchor member such as a portion of a locator wire as described in further detail below with preference to FIGS. 12-22 is one example of a structure that provides such a sealing function that controls flow of a gel or semi-gel state material.

Referring again to FIG. 1 and to FIGS. 6-7, by providing the sealing pad 10 with a first portion 12 having an uncross-linked chemical structure and a second portion 14 having a cross-linked chemical structure, the sealing pad 10 may have advantages associated with both of the sealing pads 200, 300 described above. For example, the uncross-linked collagen material of the first portion 12 may provide relatively fast and adequate sealing of the vessel puncture 114, gap 126, and entrance into the percutaneous incision 118, while the cross-linked chemical structure of the second portion 14 when expanded, provides structure within the percutaneous incision 118 that retains the sealing pad 10 in position.

Referring to FIG. 6, the sealing pad 10 is shown positioned in the percutaneous incision 118 prior to absorbing fluid. FIG. 7 illustrates the sealing pad 10 after having absorbed fluid. The first portion 12, after having changed into a gel or semi-gel state, flows into the vessel puncture 114, gap 126, and into contact with inner walls of the percutaneous incision 118. The second portion 14 expands in at least the radial direction R, and in some instances also the axial direction A into contact with the inner wall of the percutaneous incision 118 with a retention force sufficient to hold the sealing pad 10 within the percutaneous incision 118. Described in another way, providing the sealing pad with cross-linked and uncross-linked portions results in combined gelling to seal closed the vessel puncture 114 and swelling to hold the sealing pad in the percutaneous incision 118 upon hydration of the sealing pad.

The example sealing pad 10 is described above having a cross-linked or substantially cross-linked portion and an uncross-linked or substantially uncross-linked portion. More generally, the sealing pad 10 may be described as having a first portion with one cross-linked chemical structure and a second portion with a different cross-linked chemical structure. Alternatively, the sealing pad can be described as having a first portion 12 having a less cross-linked chemical structure than the cross-linked chemical structure of the second portion 14. The present disclosure encompasses any sealing pad that has one portion having a physical property that provides improved sealing of the vessel puncture 114 and a second portion having a physical property that provides improved retention of the sealing pad within the percutaneous incision. The physical properties of these portions of the sealing pad may result from different cross-linked chemical structures of the material used for each of the first and second portions.

The example sealing pad 10 illustrated with reference to FIGS. 1 and 6-7 includes a marking representing a connection point 26 between the first and second portions 12, 14. In at least some arrangements, there is no visible indicator between the first and second portions 12, 14 of the sealing pad prior to the sealing pad absorbing fluid (i.e., in an unexpanded state). In at least some arrangements, the collagen or other material used for the first and second portions 12, 14 has substantially the same appearance until such time as the sealing pad absorbs fluid. Once the sealing pad absorbs fluid, the first portion 12, which may take on a gel or semi-gel state, may have a different physical appearance than the appearance of the second portion, which maintains a generally solid or less gelled or semi-gelled state than the first portion.

The sealing pad 10 is illustrated in FIGS. 1, 6 and 7 having the first portion 12 positioned entirely distally of a distal end 22 of the second portion 14. In other arrangements, at least portions of the first portion 12 extend proximally of the distal end 22 of the second portion 14. For example, at least portions of the first portion 12 may extend around an outer surface of at least a portion of the second portion 14 as a coating or partial coating of the second portion 14. In at least one example, the distal end 22 of the second portion 14 extends distally to the distal end 18 of the first portion 12 as a core-like structure within the first portion 12. Generally, the first portion 12, which comprises a less cross-linked chemical structure than the chemical structure of the second portion 14 is positioned adjacent to the vessel puncture 114 to have a shorter path of travel to seal closed the vessel puncture 114.

In at least some arrangements, the first portion 12 extends along an entire length $L_2$ of the second portion 14. The maximum dimension $D_1$ of the first portion 12 may be greater than the maximum dimension $D_2$ of the second portion 14, or vice versa. In at least one arrangement, the first portion 12 is constructed and arranged as a core or insert of the second portion 14 and arranged to flow out of the distal end of the second portion 14 in a distal direction to seal closed the vessel puncture 114.

Figure 9:
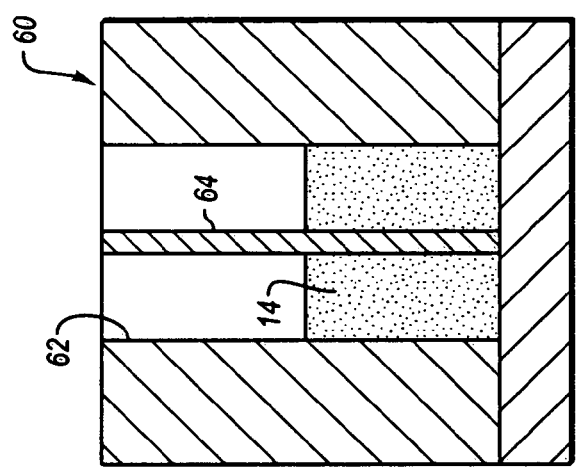
FIG. 9 is a cross-sectional view of the mold cavity of FIG. 8 filled with a first sealing pad material.
Figure 8:
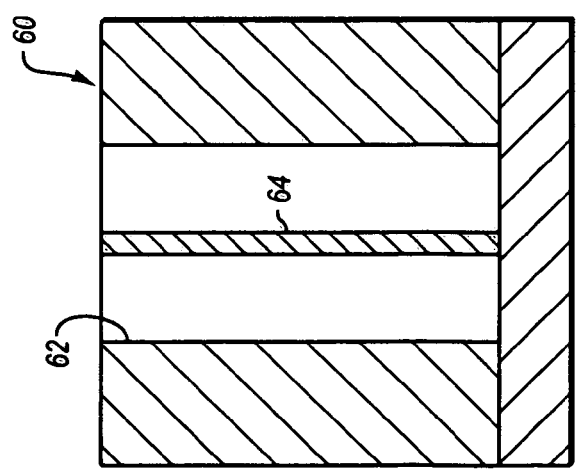
FIG. 8 is a cross-sectional view of a sealing pad mold cavity in accordance with the present disclosure.

Referring now to FIGS. 8-10, an example method of manufacturing the sealing pad 10 is shown and described. The method may include filling a mold cavity 62 of a mold 60 with a first material having a first cross-linked chemical structure. In at least one example, the material first inserted into the mold cavity 62 (the first material) is the material for the second portion 14 of the sealing pad 10. In one example, the material inserted in the mold cavity 62 is a slurry of collagen material and includes a cross-linker. The material shown in FIG. 9 is cured. In one example, the material is cured using a freeze drying technique that creates cross-linking within the material.

After the first material is cured (i.e., cross-linked or substantially cross-linked), a second material having a second cross-linked chemical structure is inserted into the mold cavity 62 in contact with the first material. In one example, the second material comprises a collagen slurry. The second material is cured. In one example, the second material is cured using a freeze drying process. The process of curing the second material may create a chemical bond between the first and second materials at the interface 26. The chemical bond may include at least some cross-linking of the collagen materials of the first and second materials which are defined now as the second and first portions 14, 16, respectively, of the sealing pad 10. In at least one example, the interface between the first and second materials includes a small gradient cross-linking zone with molecularly fused structure. This gradient cross-linking zone may provide an inseparable connection between the first and second materials (i.e., the second and first portions 14, 12). In other arrangements, a bonding material is provided at the interface 26. Some example bonding materials include, for example, adhesive or a wet collagen material.

In other arrangements, the first and second portions 12, 14 of the sealing pad 10 are formed separately as individual components and then secured together as a single piece in a later step. The first and second portions may be connected together using, for example, bonding with adhesives, wet collagen material, or other techniques.

Another manufacturing method may include dip coating one of the first and second portions 12, 14 in a liquid slurry of material for the other of the first and second portions 12, 14. For example, a core of cross-linked or substantially cross-linked collagen material may be dipped in a slurry of uncross-linked or substantially uncross-linked collagen material. Other manufacturing processes are possible.

Referring again to FIGS. 8-10, a pin 64 may be positioned within the mold cavity 62. The pin may extend along the entire length of the resulting sealing pad 10 or along only a portion of the length of the sealing pad 10. The pin 64 may define the aperture 16 in the first and second portions 12, 14 after curing of the first and second portions 12, 14. Multiple pins may be provided in alternative arrangements. Further, pins extending in other directions such as laterally across the width of the sealing pad 10 may be possible in certain designs.

Referring now to FIGS. 11-22, an example method of sealing a percutaneous incision 118 and vessel puncture 114 with a tissue puncture treatment assembly 100 is shown and described. The tissue puncture treatment assembly 100 may include a sealing pad delivery device 102 (see FIGS. 16-22), an introducer 104 (see FIGS. 11-13), a locator wire 106 (see FIGS. 11-21), and a tissue tract dilator 108 (see FIG. 15). The tissue puncture treatment assembly 100 shown and described with reference to FIGS. 11-22 is exemplary only. Other treatment devices, assemblies, and systems may benefit from the use of a sealing pad such as the sealing pad 10 described above for sealing closed a vessel puncture and percutaneous incision.

Figure 11:
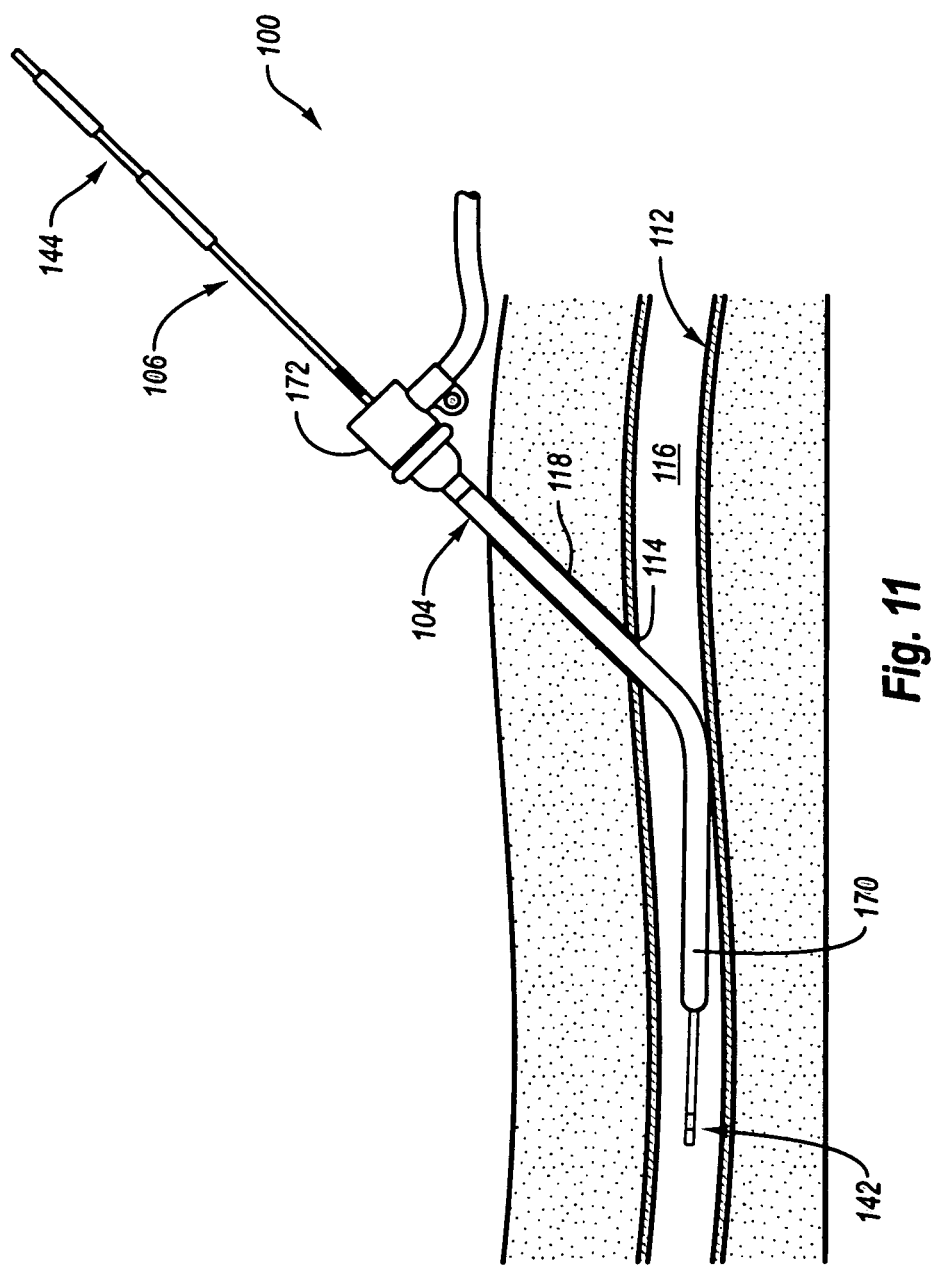
FIG. 11 is a cross-sectional view of a tissue puncture treatment assembly inserted in a vessel.

Referring now to FIG. 11, the introducer 104 is inserted through the percutaneous incision 118 and vessel puncture 114 into the vessel interior 116. A distal end portion 142 of the locator wire 106 is advanced through an opening defined in a hub 172 of the introducer 104 until passing distally beyond a distal end 170 of the introducer 104.

Figure 12:
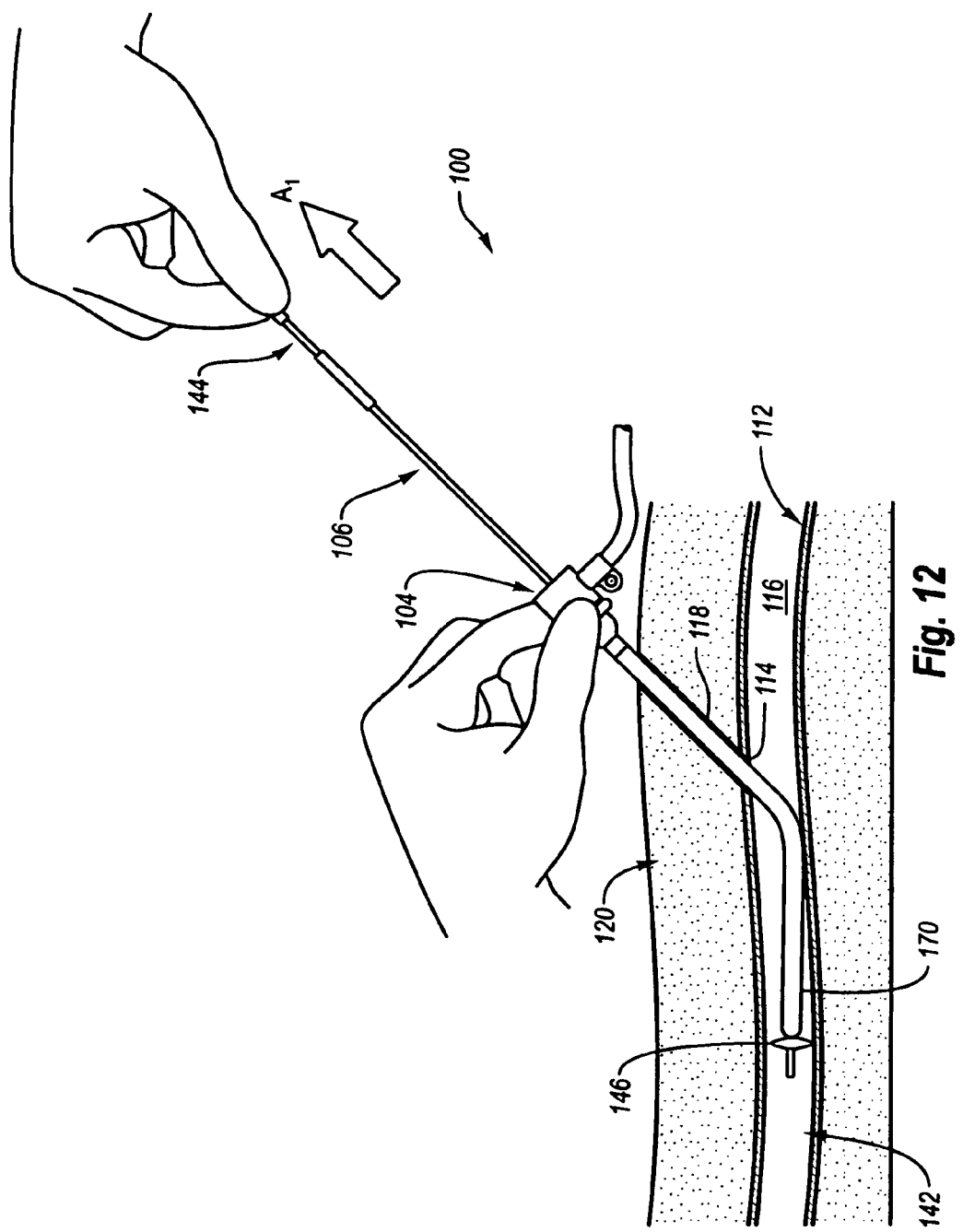
FIG. 12 is a side view of the tissue puncture treatment assembly of FIG. 11 with an anchor portion in an expanded state.

Referring now to FIG. 12, an anchor 146 at the distal end portion 142 of the locator wire 106 is activated into an expanded state using features at a proximal end portion 144 of the locator wire 106. A locator wire 106 may be retracted in a proximal direction $A_1$ until the anchor 146 contacts the distal end portion 142 of the locator wire 106.

Figure 13:
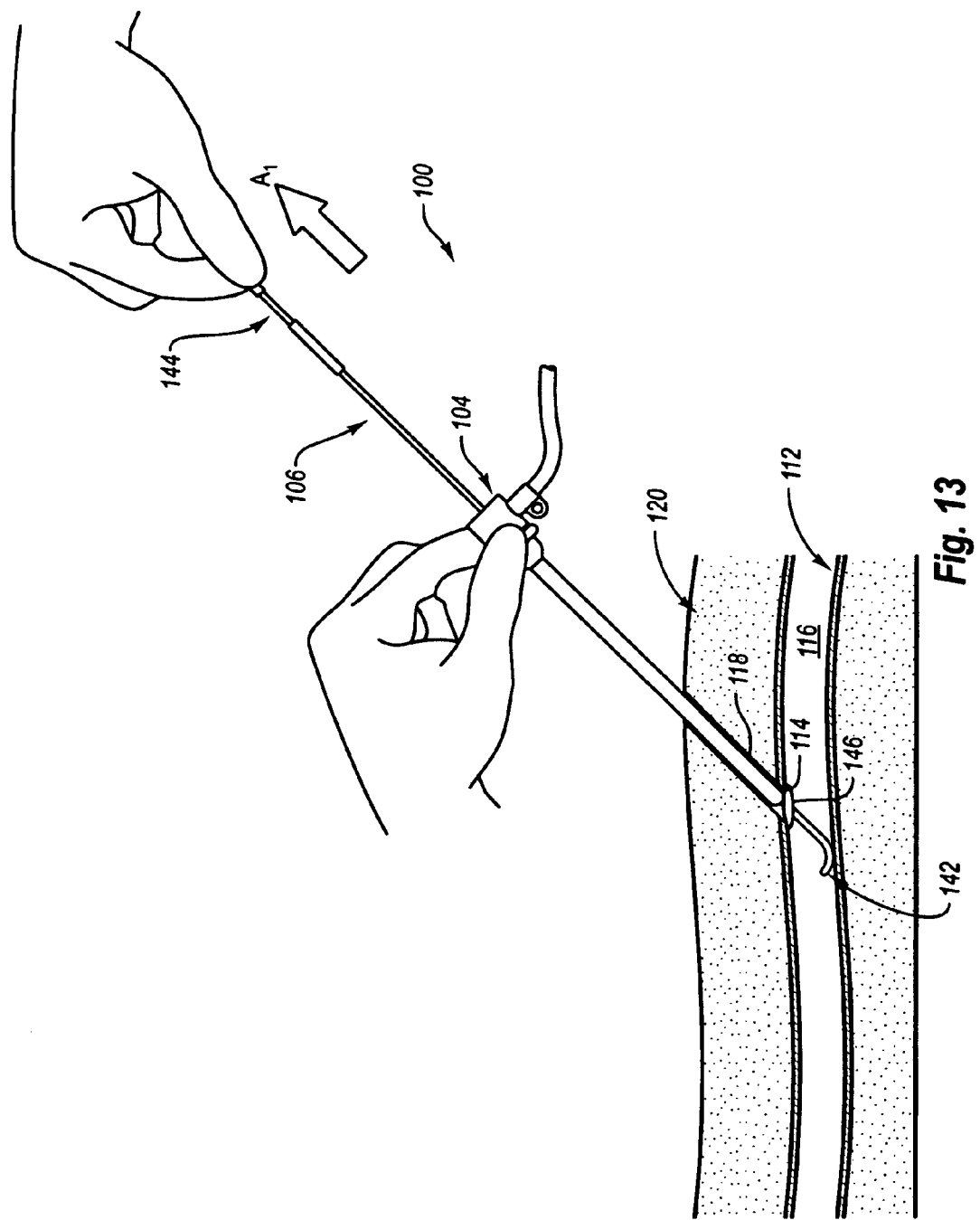
FIG. 13 is a side view of the tissue puncture treatment assembly of FIG. 12 with the expanded anchor engaged with the vessel wall adjacent to the vessel puncture.

Referring now to FIG. 13, the introducer 104 and locator wire 106 are retracted together in the proximal direction $A_1$ until the anchor 146 contacts the vessel 112 adjacent to the vessel puncture 114. The anchor 146 provides a locating function to indicate by a resistance to further retracting in the direction $A_1$ a position relative to the vessel puncture 114. The anchor 146 may also provide a stop feature on a proximal side thereof for positioning of the sealing pad 10 within the percutaneous incision 118. The anchor 146 may also provide at least partial hemostasis of the vessel puncture 114 temporarily while closing and sealing the vessel puncture 114.

Figure 14:
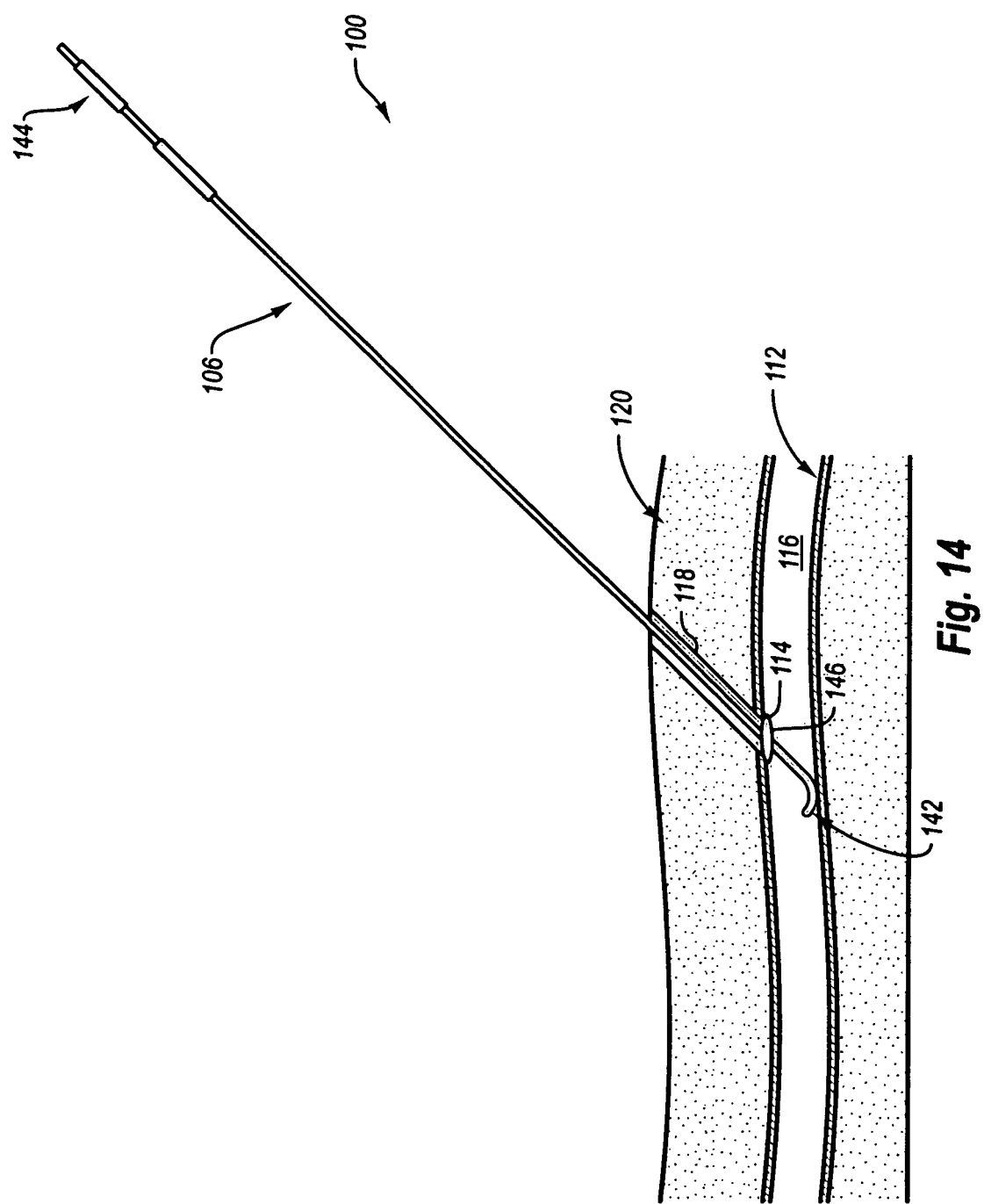
FIG. 14 is a side view of a locator wire portion of the tissue puncture treatment assembly of FIG. 13 positioned in the vessel.
Figure 15:
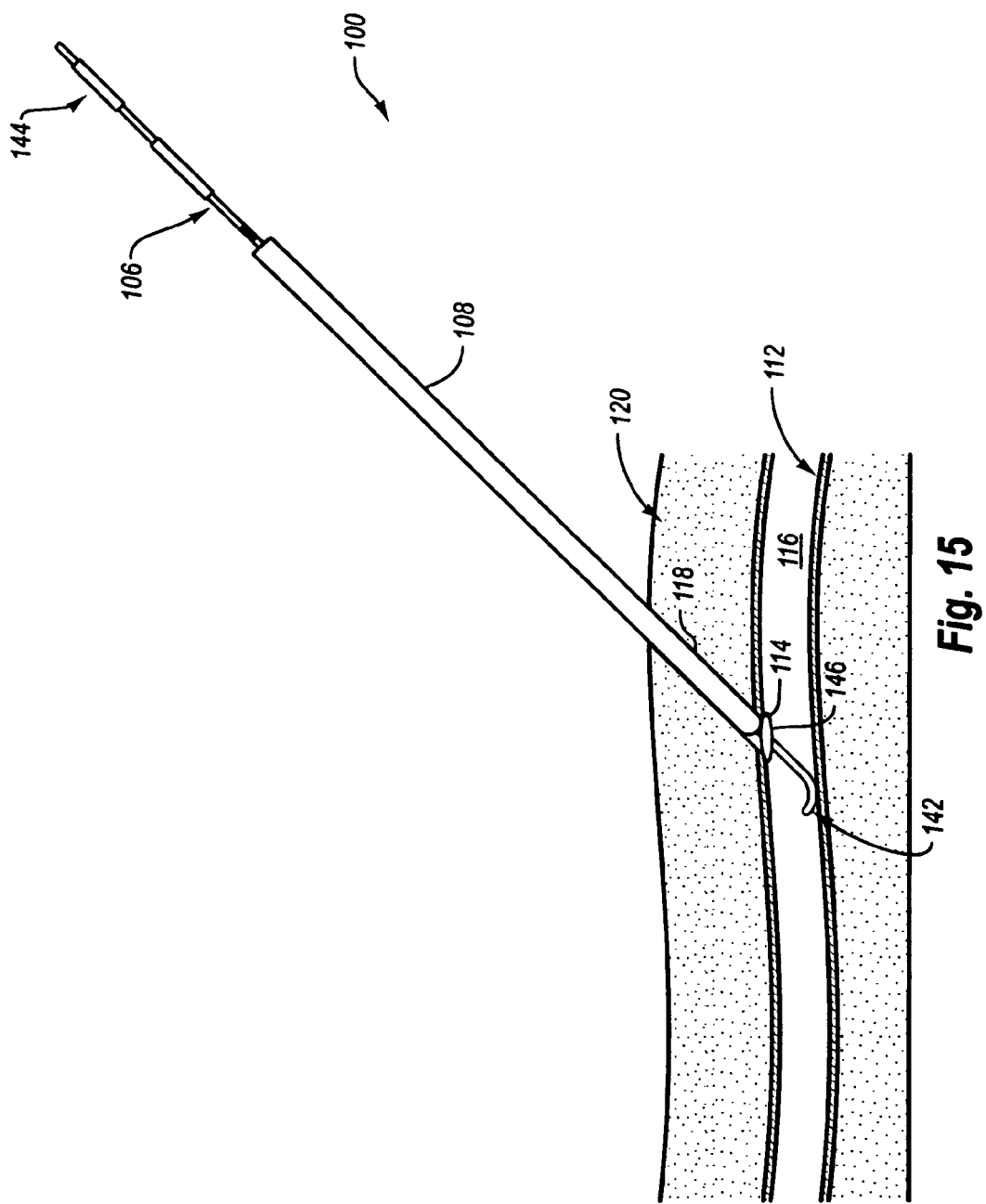
FIG. 15 is a side view of the locator wire of FIG. 14 with a dilator advanced over the locator wire into a percutaneous incision adjacent to the vessel puncture.

Referring now to FIG. 14, the introducer 104 is retracted proximally off of the locator wire 106. Referring now to FIG. 15, a dilator 108 may be advanced distally over the locator wire 106 into the percutaneous incision 118. The dilator 108 may have an outer dimension that provides at least some expansion of the percutaneous incision 118.

After expansion of the percutaneous incision 118 with the dilator 108, the dilator 108 is retracted proximally off of the locator wire 106 and a sealing pad delivery device 102 is advanced over the locator wire 106 into the percutaneous incision 118. The sealing pad delivery device 102 includes a housing 130, a carrier tube 132, a sealing pad 110 (see FIGS. 17-22), a wire locking member 134, and a tube retractor actuator 136. The sealing pad delivery device 102 is merely exemplary of many different types of devices that deliver a sealing pad into the percutaneous incision adjacent to the vessel puncture 114. Other sealing pad delivery devices might include alternative features for disposing the sealing pad within the percutaneous incision in combination with or in place of the tube retractor actuator 136 and wire locking member 134.

Figure 16:
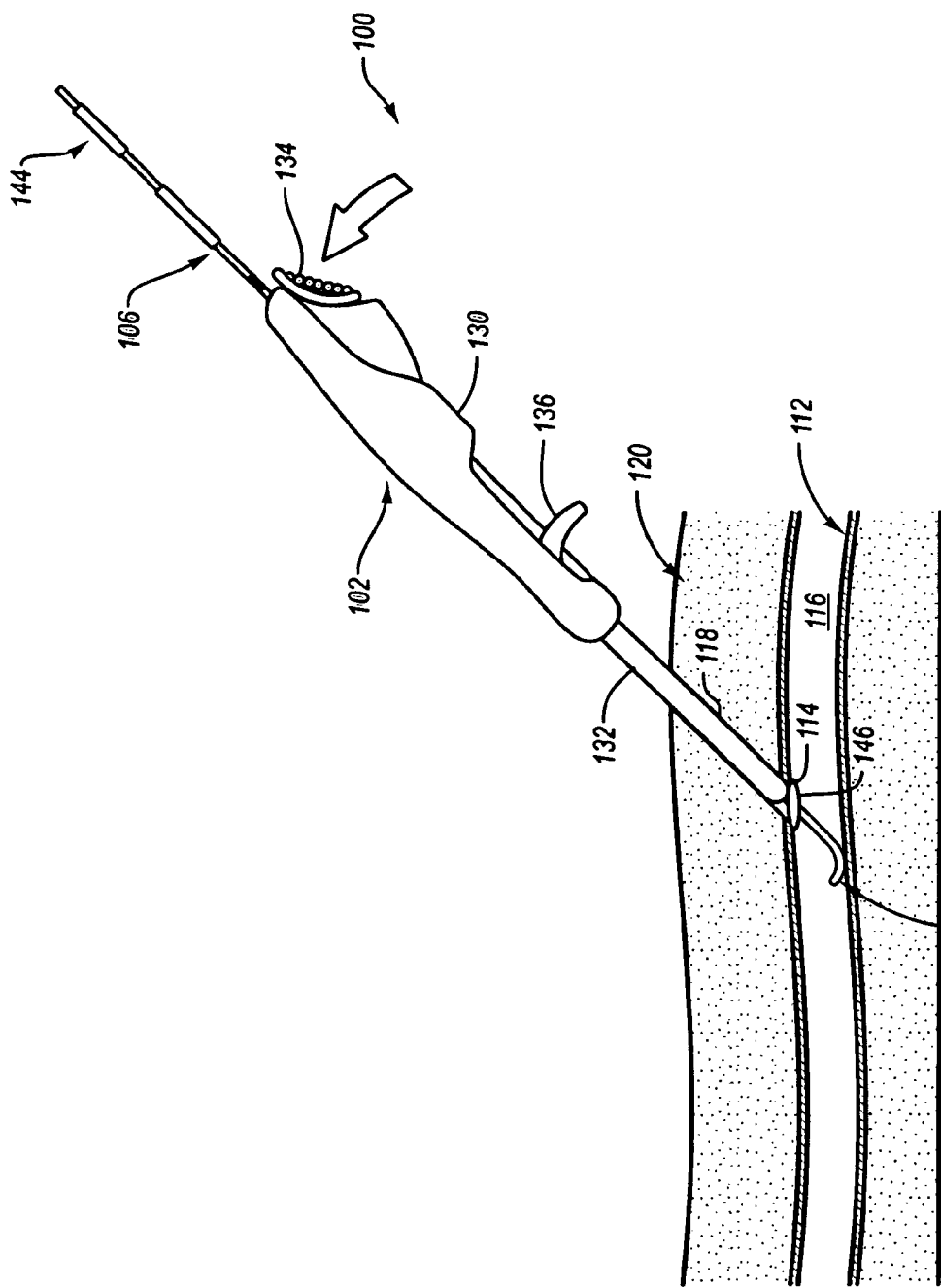
FIG. 16 is a side view of the locator wire of FIG. 14 and a sealing pad delivery device advanced over the locator wire into the percutaneous incision.

The sealing pad delivery device 102 may be maintained in a fixed axial position relative to the locator wire 106 by activating the wire locking member 134 (see FIG. 16). The wire locking member 134 may temporarily secure the sealing pad delivery device 102 to the locator wire 106 while the sealing pad 110 is disposed in the percutaneous incision 118.

Figure 17:
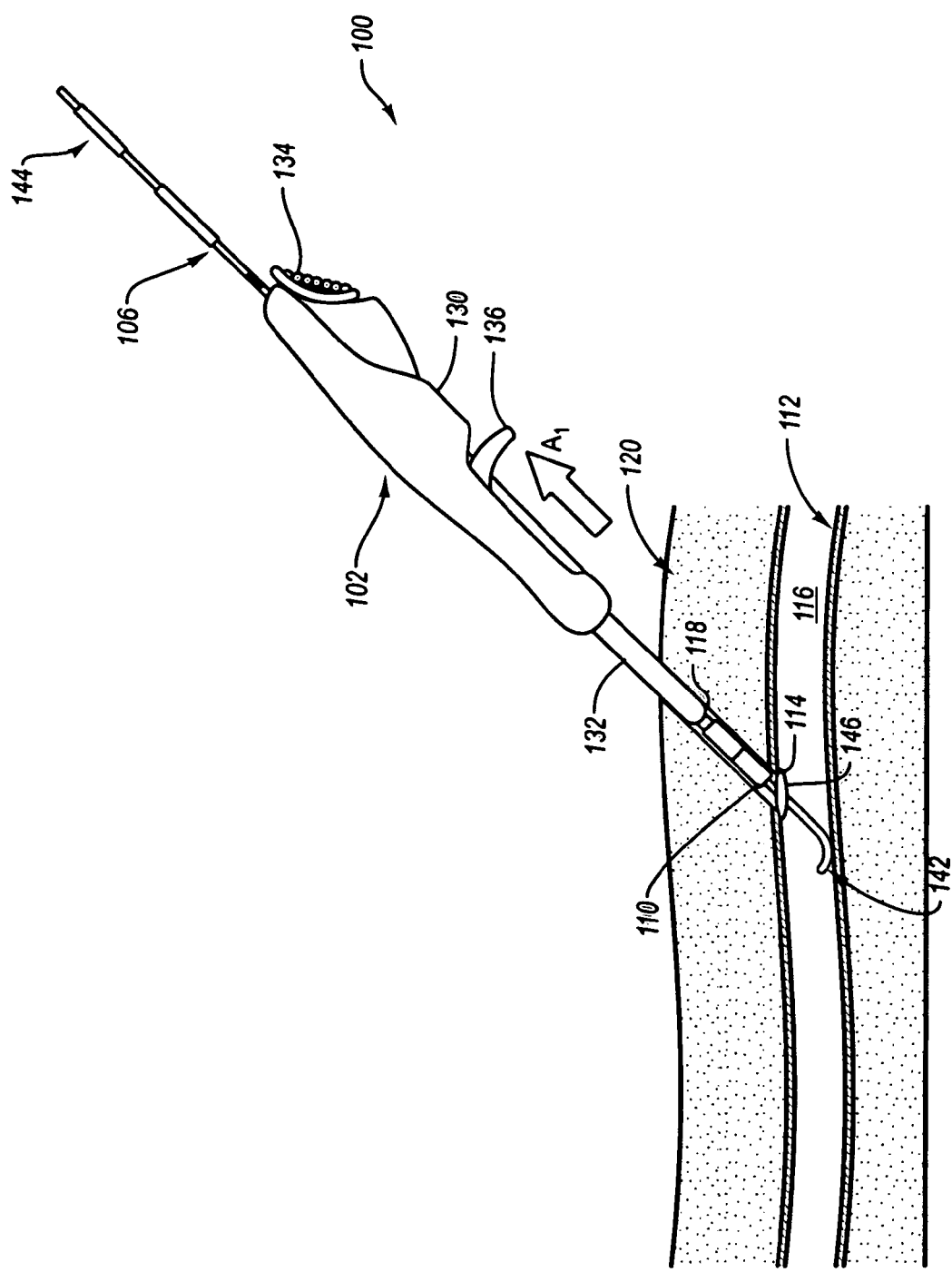
FIG. 17 is a side view of the locator wire and sealing pad delivery device of FIG. 16 with a sealing pad deployed in the percutaneous incision.

Referring to FIG. 17, the tube retractor actuator 136 is retracted proximally in the direction $A_1$ to expose the sealing pad 110 in the percutaneous incision 118. In some arrangements, the sealing pad delivery device 102 may include additional features that help maintain the sealing pad 110 in a predetermined axial position while retracting the carrier tube 132 with the tube retractor actuator 136. In some arrangements, the sealing pad delivery device 102 advances the sealing pad 110 in a distal direction instead of or in combination with retracting the carrier tube 132 in the proximal direction $A_1$.

Figure 18:
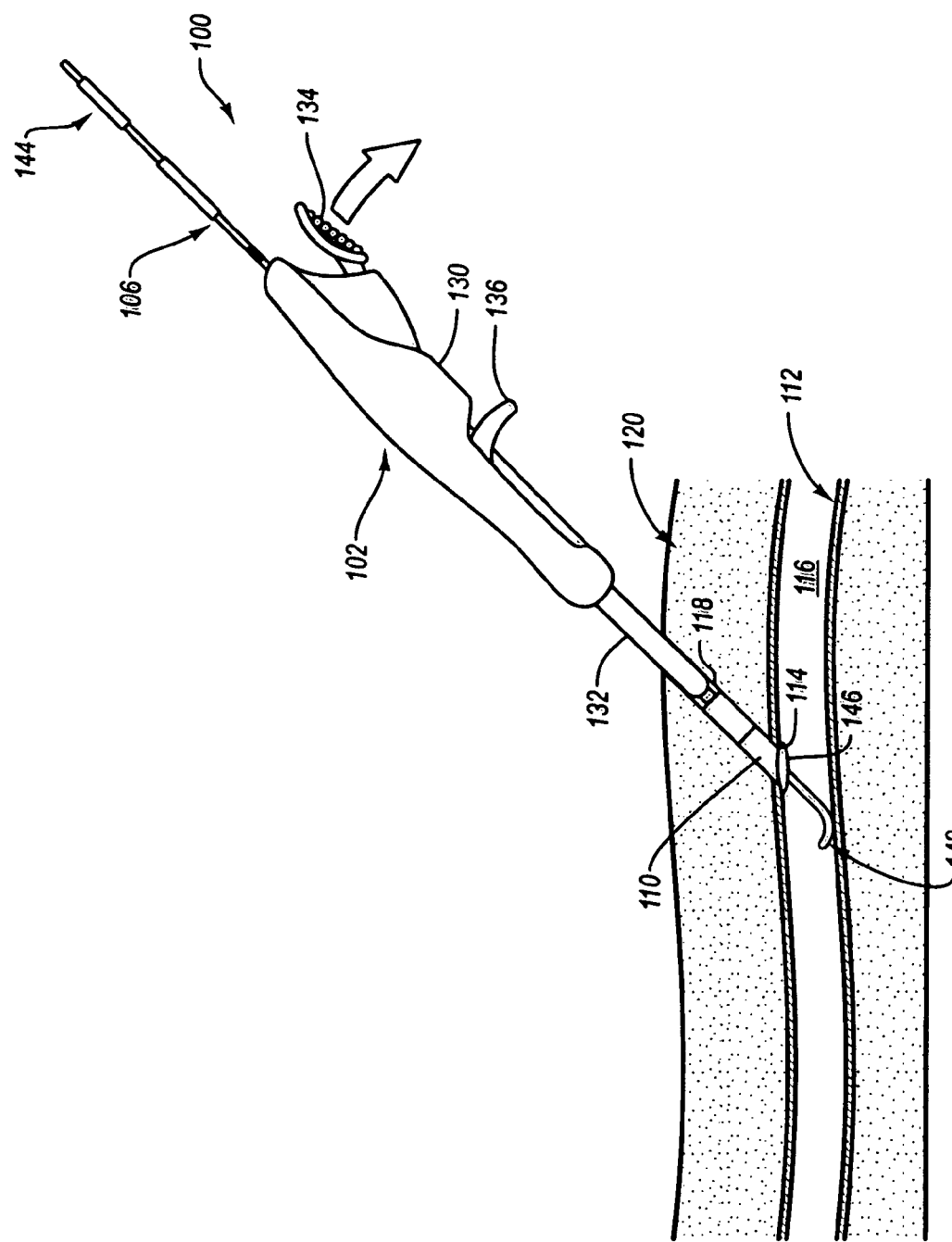
FIG. 18 is a side view of the locator wire and sealing pad delivery device of FIG. 17 with the sealing pad in an expanded state.

FIG. 18 illustrates at least partial expansion of the sealing pad 110 within the percutaneous incision 118. As described above with reference to FIGS. 1, 6 and 7, at least portions of the sealing pad 110 may seal closed the vessel puncture 114 while other portions of the sealing pad 110 may expand within the percutaneous incision 118 to help retain the sealing pad 110 within the percutaneous incision 118. The sealing pad 110 may provide such sealing and expansion by absorbing fluid. The absorbed fluid may be blood from the vessel 112. The sealing pad delivery device 102 may be released from the locator wire 106 by disengaging the wire locking member 134.

Figure 19:
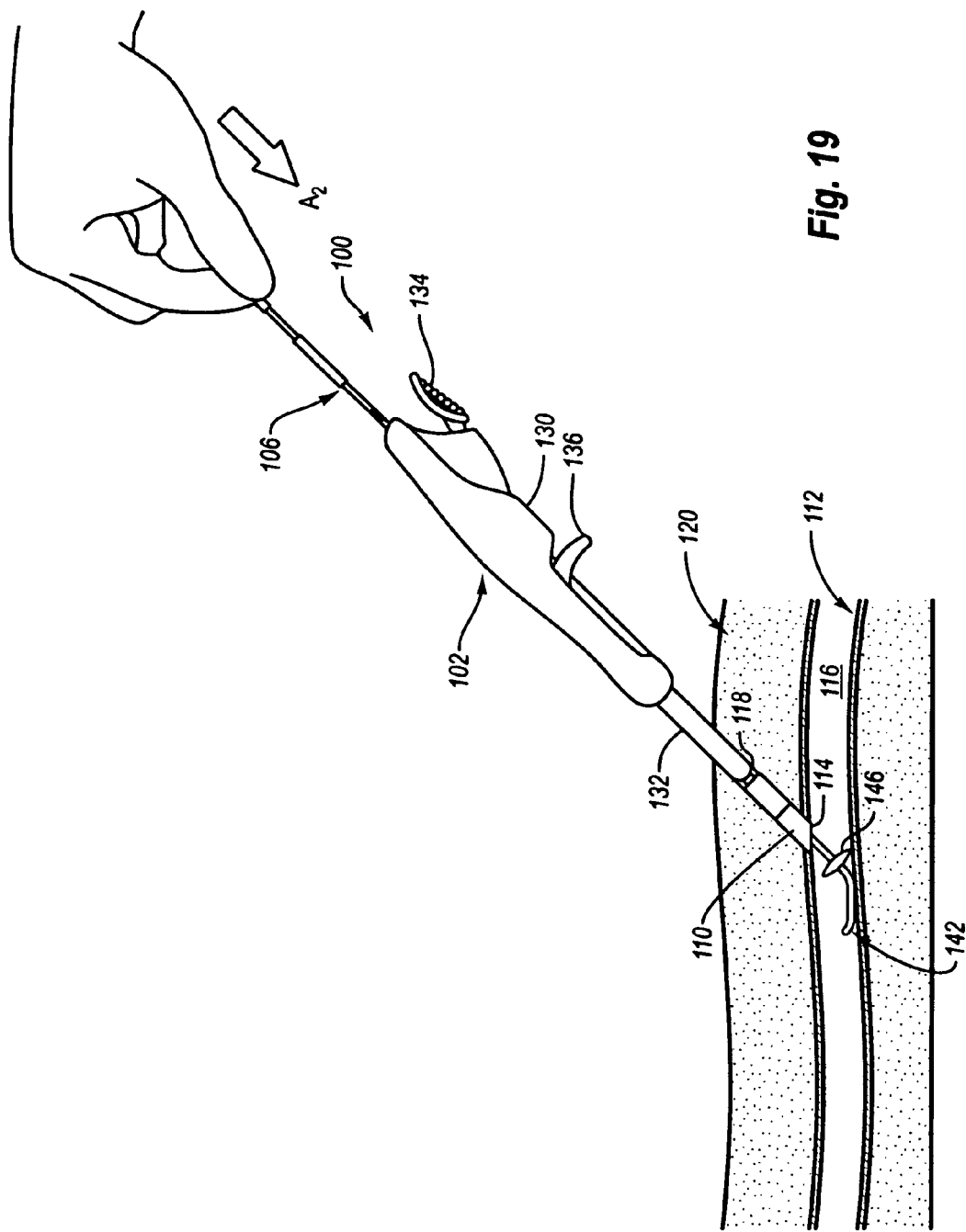
FIG. 19 is a side view of the locator wire and sealing pad delivery device of FIG. 19 with the locator wire advanced distally.
Figure 20:
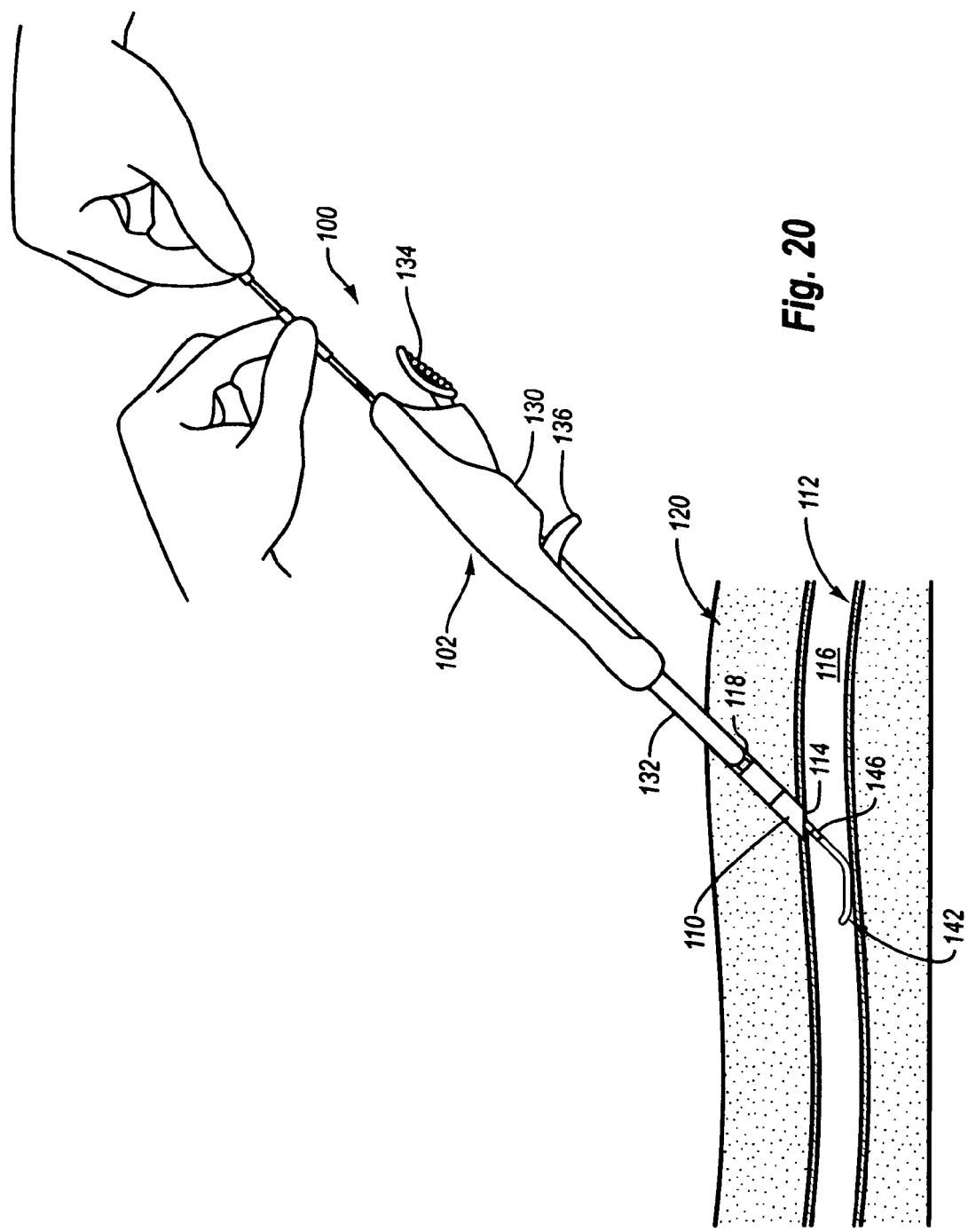
FIG. 20 is a side view of the locator wire and sealing pad delivery device of FIG. 19 with the anchor in an unexpanded state.
Figure 21:
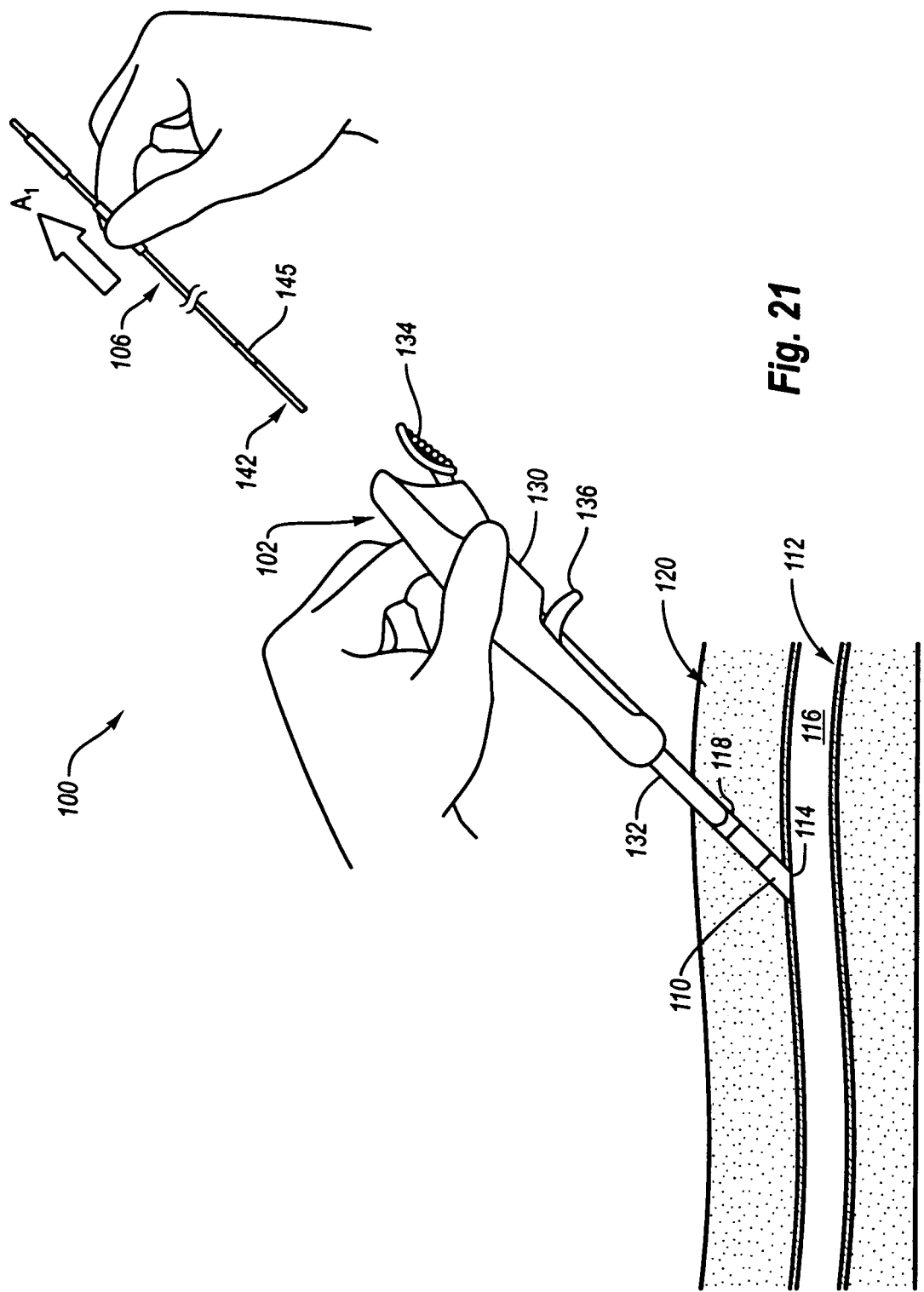
FIG. 21 is a side view of the locator wire removed proximally from the sealing pad delivery device.

Referring to FIG. 19, the locator wire 106 is advanced distally to disengage the anchor 146 from contact with the vessel 112 adjacent to the vessel puncture 114. The locator wire 106 is then actuated to return the anchor 146 to an unexpanded state that permits retraction of the distal end portion 142 of the locator wire 106 proximally through the sealing pad 110 as shown in FIGS. 20 and 21. The locator wire 106 may be retracted in the direction $A_1$ entirely from within the sealing pad delivery device 102 while the sealing pad delivery device 102 maintains position within the percutaneous incision 118. Alternatively, the locator wire 106 and sealing pad delivery device 102 may together be retracted proximally in the direction $A_1$ from the percutaneous incision 118.

Figure 22:
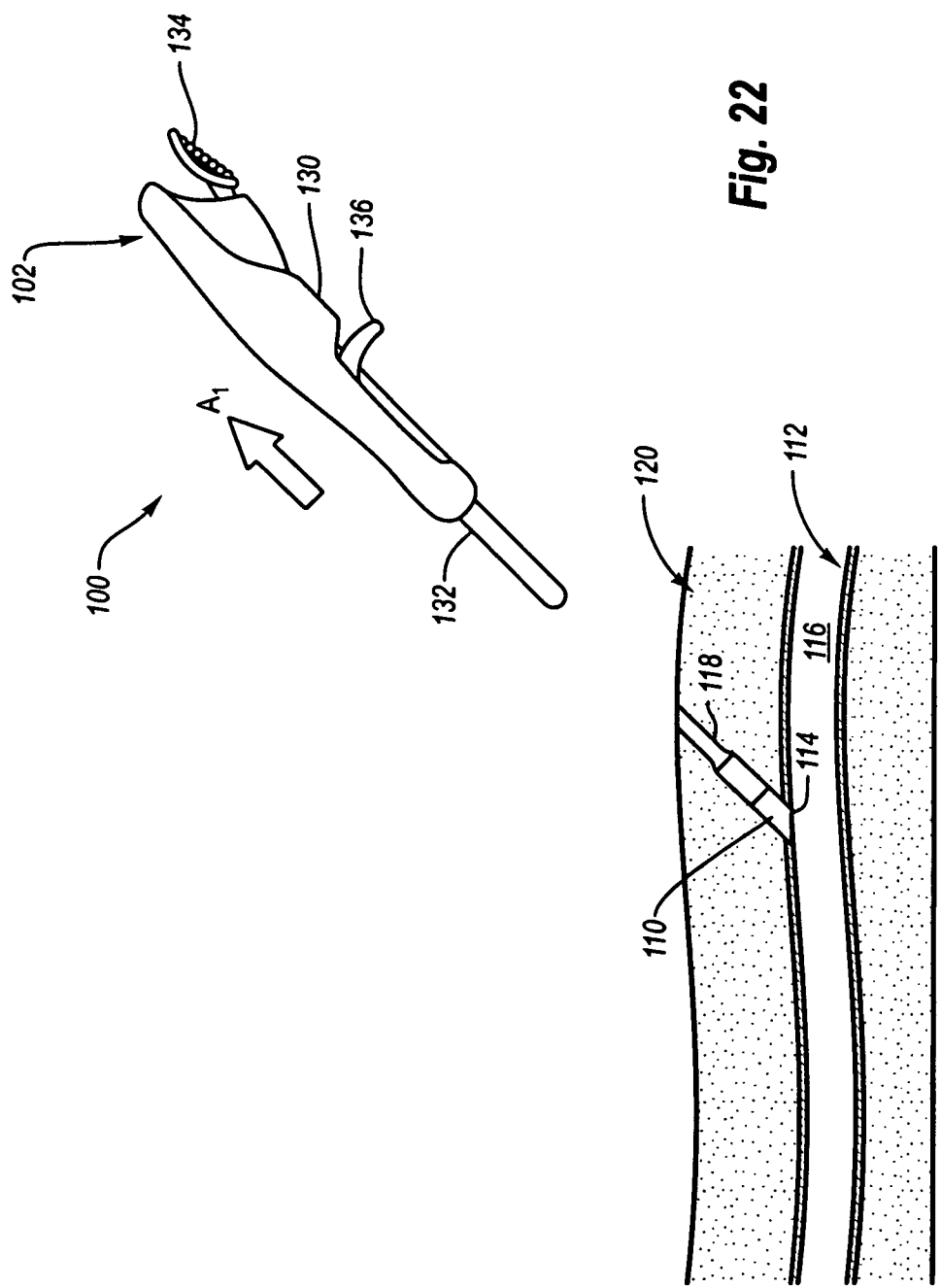
FIG. 22 is a side view of the sealing pad delivery device of FIG. 22 removed from the percutaneous incision.

FIG. 22 illustrates the sealing pad delivery device 102 retracted out of the percutaneous incision 118 with the sealing pad 110 sealing closed the vessel puncture 114 and percutaneous incision 118.

The use of a sealing pad having portions with different cross-linked chemical structure may have various advantages as discussed above. With application to the method described with reference to FIGS. 11-21, the sealing pad 110 may provide a reduction in the amount of time required to seal closed the vessel puncture 114 and percutaneous incision 118 with the tissue puncture treatment assembly 100. The sealing pad 110 may also provide improved sealing of the vessel puncture 114 and percutaneous incision 118 with limited oozing and/or hematomas.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device for partial insertion into and sealing of a tissue puncture at a vessel, comprising:
    a carrier tube having a distal end configured to be inserted into the tissue puncture in a distal direction, the distal direction extending into the tissue puncture toward an interior of the vessel;
    a sealing plug positioned in the carrier tube and arranged for ejection from the distal end of the carrier tube into the tissue puncture, the sealing plug including:
        a first collagen portion having a first portion distal-most distally-facing end surface and having a first cross-linked chemical structure;
        a second collagen portion having a distal-most end point, a proximal-most end point, a distally-facing end surface, and a second cross-linked chemical structure that is different from the first cross-linked chemical structure, wherein the first collagen portion extends along an entire length of the second collagen portion from the distal-most end point of the second collagen portion to the proximal-most end point of t second collagen portion;
        wherein at least some of the first collagen portion extends radially around an outer surface of the second collagen portion.

2. A tissue puncture closure device according to claim 1, wherein the first collagen portion is connected to the second collagen portion to define a single piece sealing plug.

3. A tissue puncture closure device according to claim 1, wherein the first collagen portion comprises a substantially uncross-linked chemical structure and the second collagen portion comprises a more cross-linked chemical structure than the first collagen portion.

4. A tissue puncture closure device according to claim 1, wherein the sealing plug includes at least one aperture that extends from a distal end to a proximal end of the sealing plug.

5. A tissue puncture closure device according to claim 1, wherein the first and second collagen portions have different lengths in a longitudinal direction.

6. A tissue puncture closure device according to claim 1, further comprising a guidewire that extends through the sealing plug and the tissue puncture.

7. A tissue puncture closure device according to claim 1, wherein the first collagen portion is configured to change into a gel or semi-gel state when exposed to liquid, and the second collagen portion is configured to expand when exposed to liquid.

8. A tissue puncture closure device for partial insertion into and sealing of a tissue puncture at a vessel, comprising:
    a carrier tube having a distal end configured to be inserted into the tissue puncture in a distal direction, the distal direction extending into the tissue puncture toward an interior of the vessel;
    a sealing plug positioned in the carrier tube and arranged for ejection from the distal end of the carrier tube into the tissue puncture, the sealing plug including:
        a first collagen portion having a distally-facing first portion distal end surface and having a first cross-linked chemical structure;
        a second collagen portion having a distally-facing second portion distal end surface and a second cross-linked chemical structure that is different from the first cross-linked chemical structure, wherein the first collagen portion extends along an entire length of the second collagen portion from a distal-most end point of the second collagen portion to a proximal-most end point of the second collagen portion, the distal-most end point being configured to be distally-must positioned on the second collagen portion when the second collagen portion is positioned in the tissue puncture, the proximal-most end point being configured to be proximally-most positioned on the second collagen portion when the second collagen portion is positioned in the tissue puncture;
        wherein at least some of the first collagen portion is held within the second collagen portion.

9. A tissue puncture closure device according to claim 8, wherein the first collagen portion is connected to the second collagen portion to define a single piece sealing plug.

10. A tissue puncture closure device according to claim 8, wherein the first collagen portion comprises a substantially uncross-linked chemical structure and the second collagen portion comprises a more cross-linked chemical structure than the first collagen portion.

11. A tissue puncture closure device according to claim 8, wherein the sealing plug includes at least one aperture that extends from a distal end to a proximal end of the sealing plug.

12. A tissue puncture closure device according to claim 8, wherein the first and second collagen portions have different lengths in a longitudinal direction.

13. A tissue puncture closure device according to claim 8, further comprising a guidewire that extends through the sealing plug and the tissue puncture.

14. A tissue puncture closure device according to claim 8, wherein the first collagen portion is configured to change into a gel or semi-gel state when exposed to liquid, and the second collagen portion is configured to expand when exposed to liquid.

* * * * *